(12) United States Patent
Miyaguchi et al.

(10) Patent No.: US 11,129,580 B2
(45) Date of Patent: Sep. 28, 2021

(54) INTRAORAL SENSOR AND METHOD FOR PRODUCING INTRAORAL SENSOR

(71) Applicant: HAMAMATSU PHOTONICS K.K., Hamamatsu (JP)

(72) Inventors: Kazuhisa Miyaguchi, Hamamatsu (JP); Shigehiro Kitamura, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 26 days.

(21) Appl. No.: 16/641,323

(22) PCT Filed: Aug. 24, 2018

(86) PCT No.: PCT/JP2018/031359
§ 371 (c)(1),
(2) Date: Feb. 24, 2020

(87) PCT Pub. No.: WO2019/044699
PCT Pub. Date: Mar. 7, 2019

(65) Prior Publication Data
US 2020/0289070 A1 Sep. 17, 2020

(30) Foreign Application Priority Data
Aug. 30, 2017 (JP) .............................. JP2017-165259

(51) Int. Cl.
*A61B 6/14* (2006.01)
*A61B 6/00* (2006.01)
(Continued)

(52) U.S. Cl.
CPC .............. *A61B 6/145* (2013.01); *A61B 6/425* (2013.01); *G01T 1/161* (2013.01); *G01T 1/20* (2013.01); *G02B 6/08* (2013.01); *A61B 2562/225* (2013.01)

(58) Field of Classification Search
CPC ........... A61B 6/145; A61B 6/425; A61B 6/14; G01T 1/141; G01T 1/20
See application file for complete search history.

(56) References Cited

U.S. PATENT DOCUMENTS

| | | | |
|---|---|---|---|
| 5,434,418 | A | 7/1995 | Schick |
| 9,357,972 | B2 | 6/2016 | Chen et al. |

(Continued)

FOREIGN PATENT DOCUMENTS

| | | | |
|---|---|---|---|
| JP | S61-225684 | A | 10/1986 |
| JP | H8-275942 | A | 10/1996 |

(Continued)

OTHER PUBLICATIONS

Internationl Preliminary Report on Patentability dated Mar. 12, 2020 for PCT/JP2018/031359.

*Primary Examiner* — Michael C Bryant
(74) *Attorney, Agent, or Firm* — Faegre Drinker Biddle & Reath LLP

(57) ABSTRACT

An intraoral sensor includes an image sensor, an FOP, a scintillator, a case, and a signal cable. The FOP includes a first main surface, a second main surface, and a plurality of lateral surfaces. The first main surface and the second main surface have a polygonal shape. An edge of the second main surface is constituted by a plurality of corner portions, and a plurality of side portions. The scintillator is provided on the second main surface and the plurality of lateral surfaces in such a manner that a second corner portion out of the plurality of corner portions and a second ridge portion are exposed. The second corner portion located on a second direction side opposite to a first direction in which the signal cable extending beyond, and the second ridge portion constituted by the lateral surfaces adjacent to the second corner portion adjacent to each other.

7 Claims, 14 Drawing Sheets

(51) Int. Cl.
  *G01T 1/161* (2006.01)
  *G01T 1/20* (2006.01)
  *G02B 6/08* (2006.01)

(56) References Cited

U.S. PATENT DOCUMENTS

| | | | |
|---|---|---|---|
| 10,130,317 B2* | 11/2018 | Miller | H01L 27/14663 |
| 2009/0033777 A1* | 2/2009 | Ligozat | H04N 3/1575 |
| | | | 348/294 |
| 2011/0135057 A1* | 6/2011 | Mori | G01T 1/2018 |
| | | | 378/62 |
| 2012/0228512 A1 | 9/2012 | van Arendonk et al. | |
| 2013/0043397 A1 | 2/2013 | Toyama et al. | |
| 2013/0129044 A1* | 5/2013 | Yoon | A61B 6/145 |
| | | | 378/62 |
| 2014/0023177 A1 | 1/2014 | Chen et al. | |
| 2014/0367578 A1 | 12/2014 | Zeller | |
| 2020/0261040 A1* | 8/2020 | Miyaguchi | A61B 1/24 |

FOREIGN PATENT DOCUMENTS

| | | |
|---|---|---|
| JP | 2009-500814 A | 1/2009 |
| JP | 2014-153074 A | 8/2014 |
| WO | WO-2007/003571 A1 | 1/2007 |

* cited by examiner

INTRAORAL SENSOR AND METHOD FOR PRODUCING INTRAORAL SENSOR

TECHNICAL FIELD

The present invention relates to an intraoral sensor and a method for manufacturing an intraoral sensor.

BACKGROUND ART

Known intraoral sensors include an image sensor, a fiber optical plate, a scintillator, a case, and a signal cable (for example, refer to Patent Literature 1). The case contains the image sensor, the fiber optical plate, and the scintillator. The signal cable is electrically connected to the image sensor, and extending beyond from the case. The scintillator is disposed on the fiber optical plate.

CITATION LIST

Patent Literature

Patent Literature 1: U.S. Pat. No. 9,357,972

SUMMARY OF INVENTION

Technical Problem

In the intraoral sensor, typically, the fiber optical plate has a polygonal shape in a plan view. An outer edge of the fiber optical plate and an outer edge of the scintillator match each other when viewed from a direction orthogonal to the fiber optical plate. In a case where impact is applied to the intraoral sensor from the outside, the impact is transferred to the scintillator through the case. In this case, there is a concern that in the scintillator, a portion located on a corner of the fiber optical plate may be peeled off from the fiber optical plate. When the scintillator is peeled off from the fiber optical plate, reliability of the intraoral sensor deteriorates.

In a case where the intraoral sensor includes the signal cable, in the case, a portion opposite to a direction in which the signal cable extending beyond is susceptible to the impact. The impact is likely to be transferred to the scintillator located on a corner opposite to the direction, in which the signal cable extending beyond, out of corners of the fiber optical plate. Accordingly, the scintillator located on the corner on the opposite side is likely to be peeled off from the fiber optical plate.

In the intraoral sensor disclosed in Patent Literature 1, the shape of the case is set in such a manner that a gap between the case and the fiber optical plate is enlarged at a position corresponding to the corner on the opposite side. Accordingly, impact from the outside is less likely to be transferred to the scintillator. However, in a case where the shape of the case is set as described above, an external shape of the case is large, and thus it is difficult to avoid an increase in size of the intraoral sensor.

An object of a first aspect of the invention is to provide an intraoral sensor in which an improvement of reliability and suppression of an increase in size are compatible. An object of a second aspect of the invention is to provide a method for manufacturing the intraoral sensor in which the improvement of the reliability and the suppression of the increase in size are compatible.

Solution to Problem

A first aspect of the invention provides an intraoral sensor including an image sensor including a light detection region a fiber optical plate; a scintillator; a case; and a signal cable. The fiber optical plate is disposed on the image sensor to cover the light detection region. The scintillator is disposed on the fiber optical plate. The case contains the image sensor, the fiber optical plate, and the scintillator. The signal cable is electrically connected to the image sensor and extending beyond from the case. The fiber optical plate includes a first main surface, a second main surface, and a plurality of lateral surfaces. The first main surface opposes the image sensor and has a polygonal shape. The second main surface opposes the scintillator and has a polygonal shape. The plurality of lateral surfaces connect an edge of the first main surface and an edge of the second main surface. The edge of the second main surface is constituted by a plurality of corner portions and a plurality of side portions. The plurality of side portions connect the corner portions adjacent to each other. The scintillator is provided on the second main surface and the plurality of lateral surfaces in such a manner that a corner portion located on a second direction side opposite to a first direction in which the signal cable extending beyond out of the plurality of corner portions and a ridge portion are exposed. The ridge portion constituted by the lateral surfaces adjacent to the corner portion located on the second direction side and adjacent to each other.

In the first aspect, the scintillator is provided on the second main surface and the plurality of lateral surfaces in such a manner that the corner portion and the ridge portion located on the second direction side, in the fiber optical plate are exposed. That is, the scintillator is not located on the corner portion and the ridge portion located on the second direction side in the fiber optical plate. Accordingly, even in a case where a portion on the second direction side in the case receives impact from the outside, the impact is less likely to be transferred to the scintillator, and thus the scintillator is less likely to be peeled off. As a result, in the first aspect, it is not necessary to enlarge an external shape of the case to suppress peeling-off of the scintillator, and thus an increase in size of the intraoral sensor is suppressed. As described above, the scintillator is less likely to be peeled off. As a result, in the first aspect, reliability of the intraoral sensor is improved.

In the first aspect, the scintillator may be provided on the second main surface and the plurality of lateral surfaces in such a manner that a corner portion located on the first direction side out of the plurality of corner portions and a ridge portion are also exposed. The ridge portion constituted by the lateral surfaces adjacent to the corner portion located on the first direction side and adjacent to each other.

In a case where the intraoral sensor includes a signal cable, there is a concern that not only a portion on the second direction side in the case and a portion on the first direction side in the case may receive impact. In this case, there is a concern that the impact received from the portion on the first direction side in the case may be transferred to the scintillator, and the scintillator may be peeled off from the fiber optical plate.

In a case where the scintillator is provided on the second main surface and the plurality of lateral surfaces in such a manner that the corner portion and the ridge portion located on the first direction side in the fiber optical plate are exposed, the scintillator is not located on the corner portion and the ridge portion located on the first direction side in the fiber optical plate. Accordingly, even in a case where the portion on the first direction side in the case receives impact from the outside, the impact is less likely to be transferred to the scintillator, and thus the scintillator is less likely to be peeled off. As a result, in the first aspect, it is not necessary to enlarge an external shape of the case to suppress peeling-off of the scintillator, and thus an increase in size of the intraoral sensor is suppressed. As described above, the scintillator is less likely to be peeled off. As a result, in the first aspect, reliability of the intraoral sensor is improved.

In the first aspect, the scintillator may be formed from a scintillator material containing CsI as a main component. In this case, the scintillator can be formed by vapor deposition, and thus it is possible to easily provide the scintillator.

The first aspect may further include a buffer material. In this case, the buffer material is disposed between an end of a structure in the second direction and the case, and contacting with the structure. The structure includes the image sensor, the fiber optical plate, and the scintillator. The buffer material is in contact with the structure. According to this configuration, impact which the intraoral sensor receives from the outside is less likely to be transferred to the scintillator. Accordingly, peeling-off of the scintillator is more reliably suppressed.

A second aspect of the invention provides a method for manufacturing an intraoral sensor. The intraoral sensor includes a structure including an image sensor, a fiber optical plate, and a scintillator, a case, and a signal cable. The case contains the structure. The signal cable is electrically connected to the image sensor and extending beyond from the case. In the second aspect, the fiber optical plate including a first main surface, a second main surface, and a plurality of lateral surfaces is prepared, and the scintillator is provided on the second main surface and the plurality of lateral surfaces. The first main surface has a polygonal shape. The second main surface is opposite to the first main surface, and has a polygonal shape. The plurality of lateral surfaces connect an edge of the first main surface and an edge of the second main surface. The edge of the second main surface is constituted by a plurality of corner portions, and a plurality of side portions connecting the corner portions adjacent to each other. When providing the scintillator on the second main surface and the plurality of lateral surfaces, a corner portion located on a second direction side opposite to a first direction in which the signal cable extending beyond out of the plurality of corner portions and a ridge portion are exposed. The ridge portion constituted by the lateral surfaces adjacent to the corner portion located on the second direction side and adjacent to each other.

In the second aspect, the scintillator is provided on the second main surface and the plurality of lateral surfaces in such a manner that the corner portion and the ridge portion located on the second direction side, in the fiber optical plate are exposed. Accordingly, as described above, it is possible to obtain the intraoral sensor in which an increase in size is suppressed and reliability is improved.

In the second aspect, when providing the scintillator, may cover the corner portion located on the second direction side with a jig supporting the fiber optical plate, and may vapor depositing a scintillator material constituting the scintillator with the jig as a mask. According to this, a process of manufacturing the intraoral sensor is simplified.

In the second aspect, the scintillator material may contain CsI as a main component. In this case, formation of the scintillator by vapor deposition becomes simple.

Advantageous Effects of Invention

According to the first aspect of the invention, an intraoral sensor in which an improvement of reliability and suppression of an increase in size are compatible is provided. According to the second aspect of the invention, a method for manufacturing the intraoral sensor in which the improvement of the reliability and the suppression of the increase in size are compatible is provided.

DESCRIPTION OF EMBODIMENTS

Figure 1:
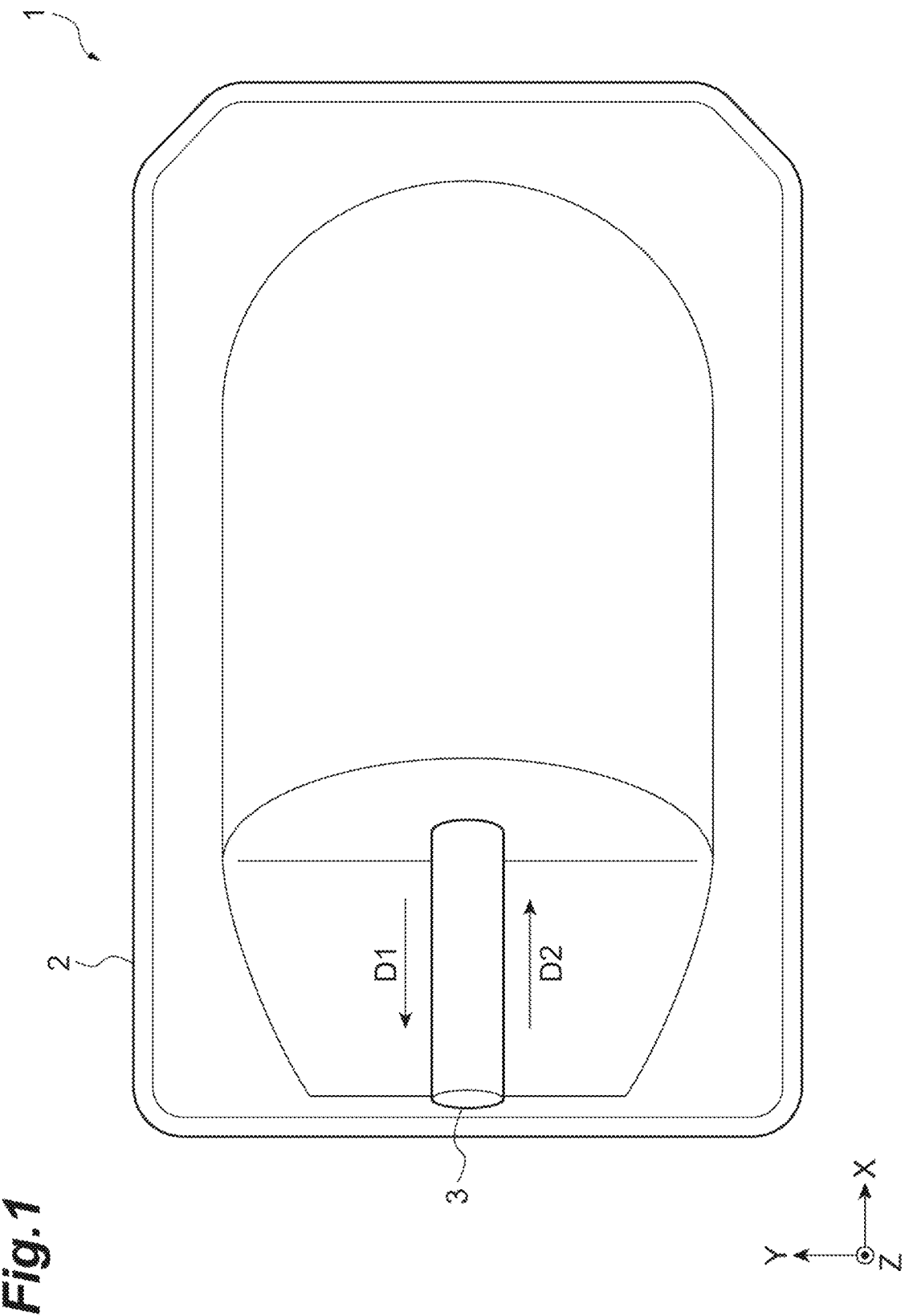
FIG. 1 is a plan view of an intraoral sensor according to an embodiment.

Hereinafter, an embodiment of the invention will be described in detail with reference to the accompanying drawings. In description, the same reference numeral will be given to the same element or an element having the same function, and redundant description will be omitted.

Figure 2:
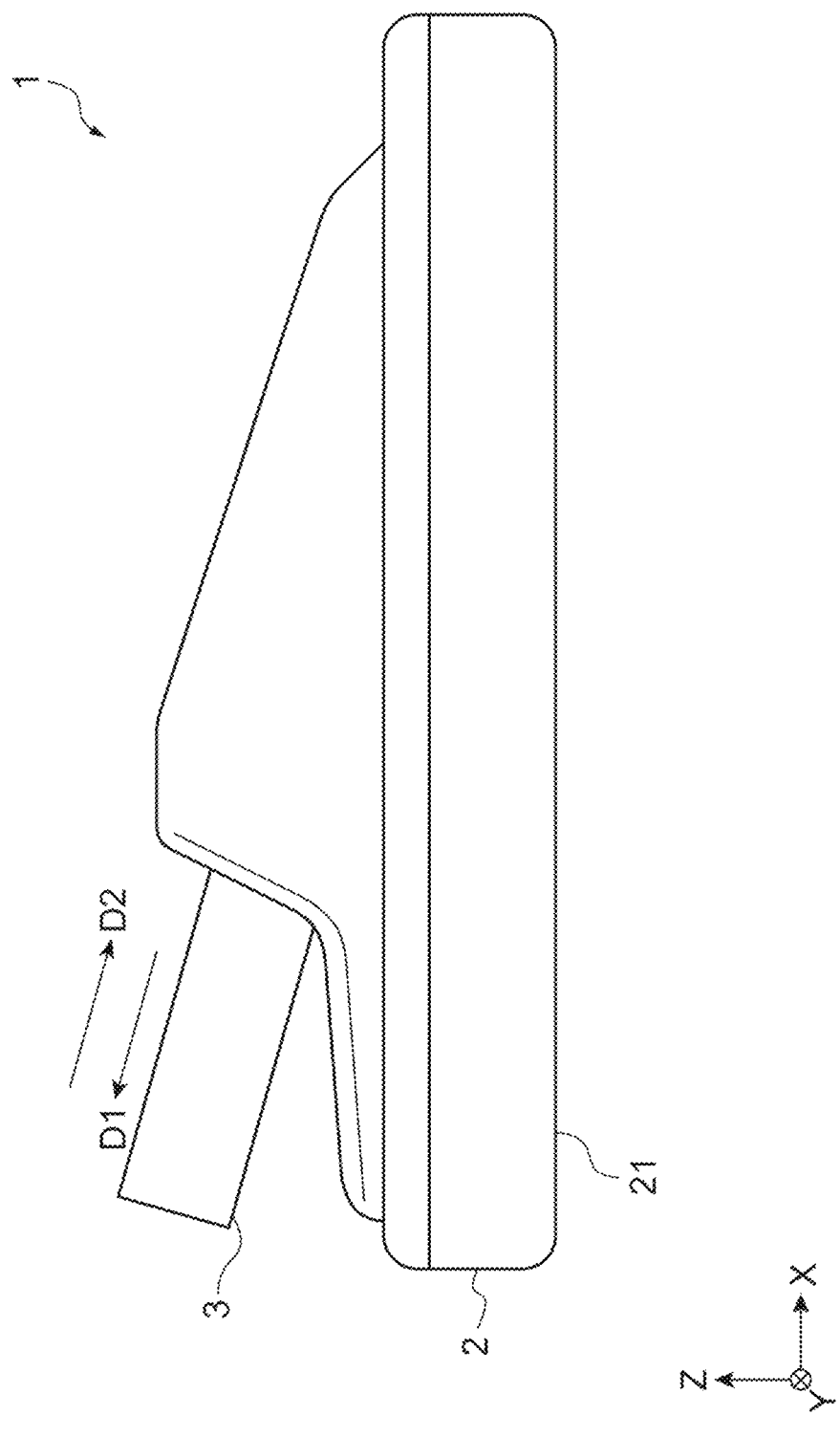
FIG. 2 is a front view of the intraoral sensor.
Figure 3:
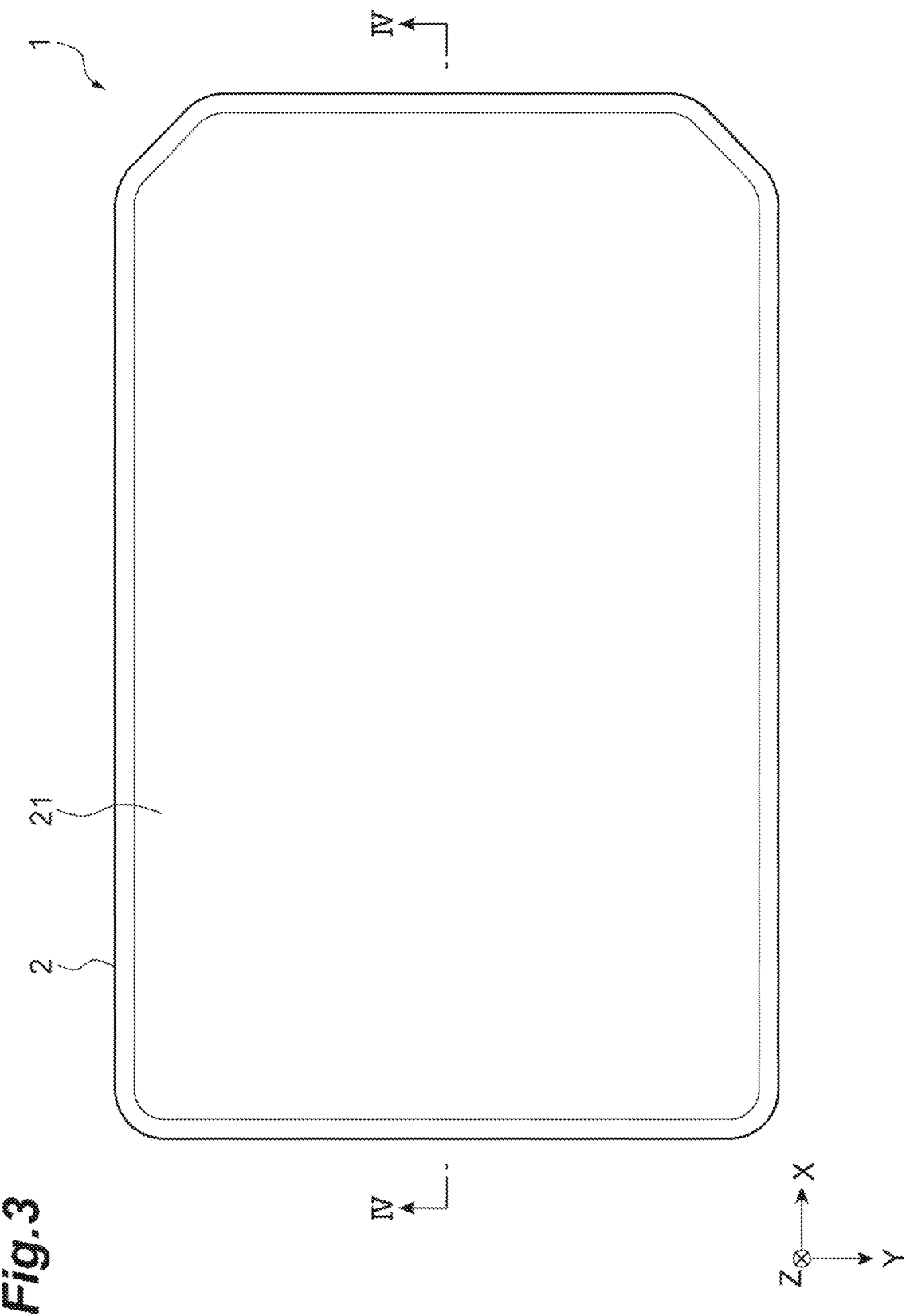
FIG. 3 is a bottom view of the intraoral sensor.
Figure 4:
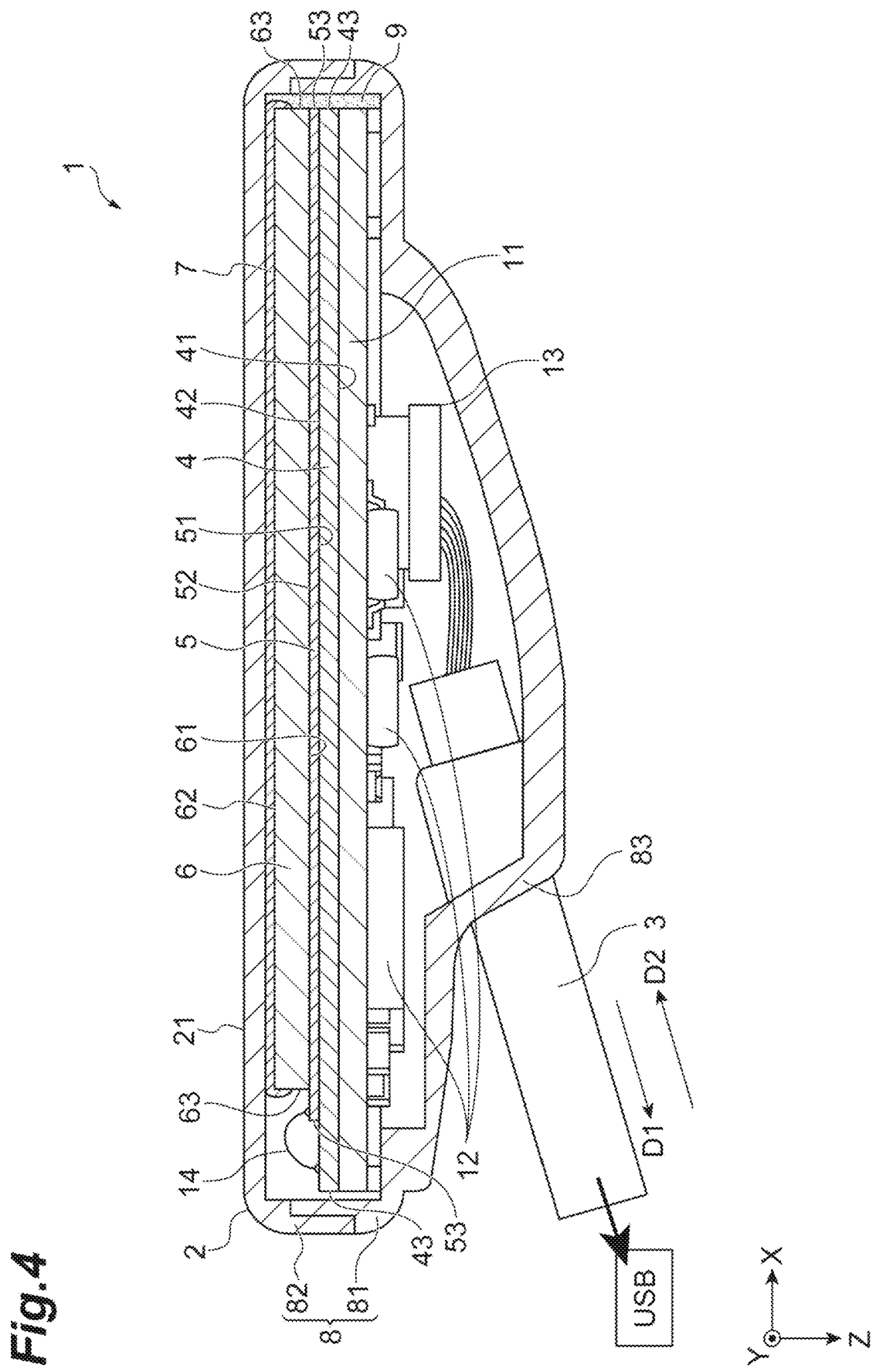
FIG. 4 is a cross-sectional view taken along line IV-IV in FIG. 3.
Figure 5:
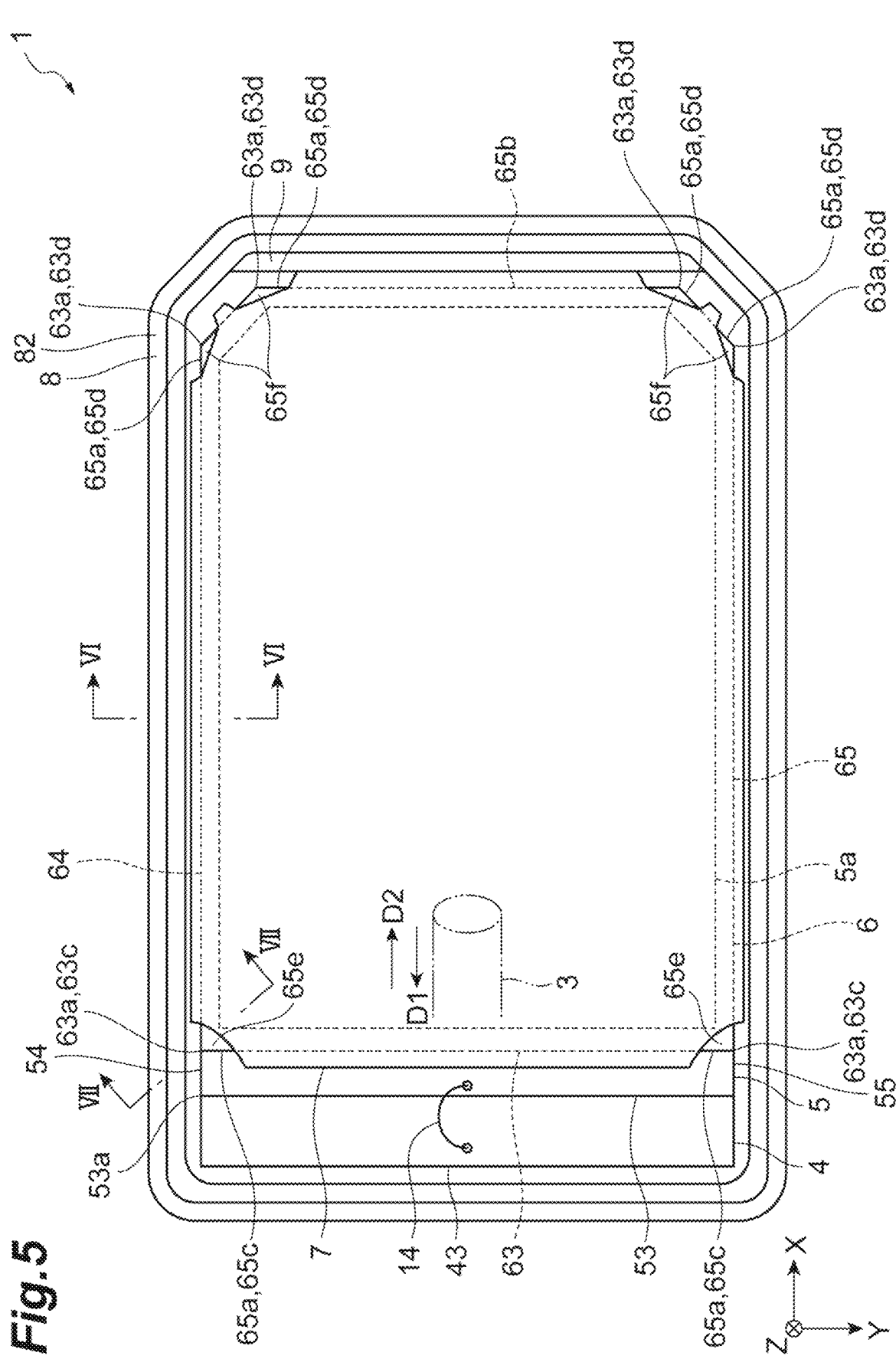
FIG. 5 is a view illustrating an internal structure of the intraoral sensor.
Figure 6:
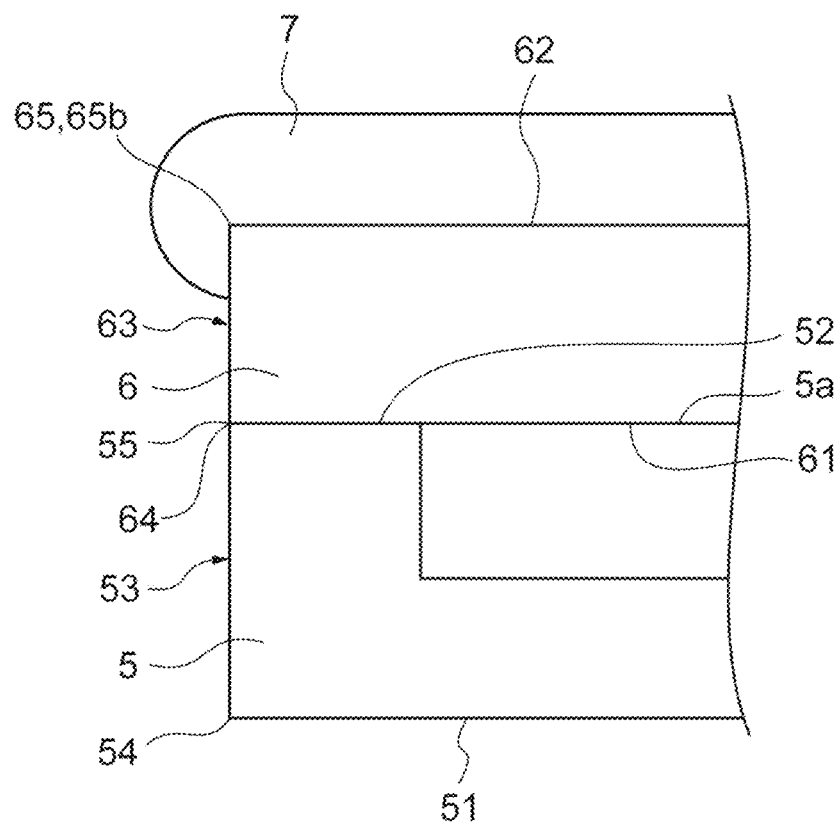
FIG. 6 is a cross-sectional view taken along line VI-VI in FIG. 5.
Figure 7:
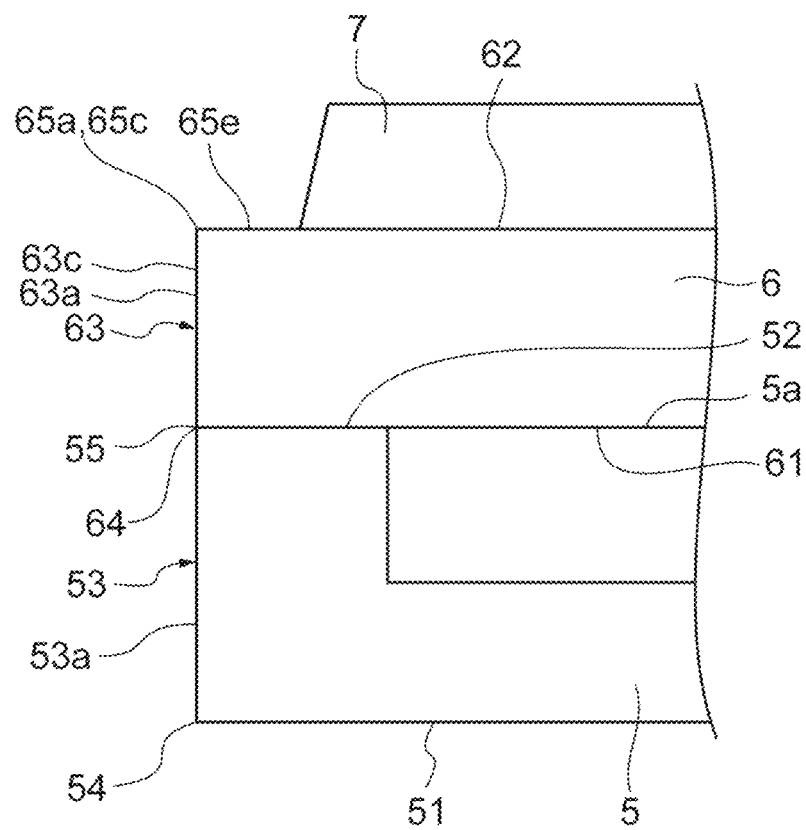
FIG. 7 is a cross-sectional view taken along line in FIG. 5.

A configuration of an intraoral sensor 1 according to this embodiment will be described with reference to FIG. 1 to FIG. 7. FIG. 1 is a plan view of the intraoral sensor 1 according to this embodiment. FIG. 2 is a front view of the intraoral sensor 1. FIG. 3 is a bottom view of the intraoral sensor 1. FIG. 4 is a cross-sectional view taken along line IV-IV in FIG. 3. FIG. 5 is a view illustrating an internal structure of the intraoral sensor 1. FIG. 6 is a cross-sectional view taken along line VI-VI in FIG. 5. FIG. 7 is a cross-sectional view taken along line VII-VII in FIG. 5.

As illustrated in FIG. 1 to FIG. 3, the intraoral sensor 1 includes a main body portion 2 and a signal cable 3. The main body portion 2 includes a detection surface 21. As illustrated in FIG. 4, the main body portion 2 includes a support substrate 4, an image sensor 5, a fiber optical plate (FOP) 6, a scintillator 7, a wiring substrate 11, an IC 12, a connector 13, a case 8, and a buffer material 9.

As illustrated in FIG. 4 and FIG. 5, the support substrate 4 has a polygonal plate shape. The support substrate 4 includes a first main surface 41, a second main surface 42, and a plurality of lateral surfaces 43. The first main surface 41 has a polygonal shape. For example, the first main surface 41 has a hexagonal shape. The second main surface 42 has a polygonal shape. For example, the second main surface 42 has a hexagonal shape. In this embodiment, the support substrate 4 includes six lateral surfaces 43.

The wiring substrate 11 is disposed on the first main surface 41. The IC 12 and the connector 13 are disposed on the wiring substrate 11. A wire and the image sensor 5 are disposed on the second main surface 42. For example, the wire is a circuit of an A/D converter. The FOP 6 is disposed on the image sensor 5. The scintillator 7 is disposed on the FOP 6. For example, a material of the support substrate 4 is glass or Si.

The case 8 contains the support substrate 4, the image sensor 5, the FOP 6, the scintillator 7, the wiring substrate 11, the IC 12, and the connector 13. An internal space of the case 8 is formed along an outer edge of a structure including the image sensor 5, the FOP 6, and the scintillator 7 when viewed from a Z-axis direction orthogonal to the first main surface 41 and the second main surface 42.

The case 8 includes a first case 81 and a second case 82. A fixing portion 83 that fixes the signal cable 3 is provided in the first case 81. A through-hole into which the signal cable 3 is inserted and fixed is formed in the fixing portion 83. The first case 81 and the second case 82 are engaged with each other. Examples of a material of the case 8 is ABS resin having impact resistance, or the like.

The signal cable 3 is fixed to the fixing portion 83 of the case 8. The signal cable 3 includes a plurality of wires through which a predetermined electric signal passes, and a clad disposed at the periphery of the plurality of wires. For example, the clad is formed from a polyvinyl chloride (PVC). The signal cable 3 is inserted into the through-hole formed in the fixing portion 83 and reaches the internal space of the case 8. When the clad is inserted into the through-hole formed in the fixing portion 83 and is fixed therein, the signal cable 3 is fixed to the case 8.

The signal cable 3 extends beyond from the case 8. The signal cable 3 extends beyond from the case 8 to protrude from the case 8. The signal cable 3 extends beyond from the case 8 along a first direction D1. The first direction D1 intersects the detection surface 21. The first direction D1 has a predetermined angle with respect to the detection surface 21. For example, an angle between the first direction D1 and the detection surface 21 is 23°. The first direction D1 is along an X-axis orthogonal to the Z-axis when viewed from the Z-axis direction.

Next, an internal structure of the intraoral sensor 1 will be described with reference to FIG. 4 and FIG. 5. The image sensor 5 is a CMOS image sensor. The image sensor 5 has a polygonal plate shape. The image sensor 5 includes a first main surface 51, a second main surface 52, and a plurality of lateral surfaces 53. The first main surface 51 opposes the support substrate 4. The first main surface 51 has a polygonal shape. For example, the first main surface 51 has a hexagonal shape. The second main surface 52 opposes the FOP 6. The second main surface 52 has a polygonal shape. For example, the second main surface 52 has a hexagonal shape. In this embodiment, the image sensor 5 includes six lateral surfaces 53.

An edge 54 of the first main surface 51 and an edge 55 of the second main surface 52 overlap each other when viewed from the Z-axis direction that is a direction orthogonal to the first main surface 51 and the second main surface 52. Each of the lateral surfaces 53 connects the edge 54 of the first main surface 51 and the edge 55 of the second main surface 52. The lateral surfaces 53 adjacent to each other constitute a plurality of ridge portions 53a. In this embodiment, the image sensor 5 includes six ridge portions 53a.

For example, a width of the image sensor 5 in the X-axis direction is 33.92 mm. For example, a width of the image sensor 5 in a Y-axis direction orthogonal to the Z-axis and the X-axis is 21.6 mm. For example, the thickness of the image sensor 5 is several μm to several tens of μm. When viewed from the Z-axis direction, the lateral surface 53 of the image sensor 5 on a first direction D1 side is provided on an inner side in comparison to the lateral surface 43 of the support substrate 4. When viewed from the Z-axis direction, another lateral surface 53 of the image sensor 5 overlap another lateral surface 43 of the support substrate 4.

The image sensor 5 includes a light detection region 5a. The light detection region 5a is constituted by a plurality of pixels. The plurality of pixels are two-dimensionally arranged with a predetermined pixel pitch. The light detection region 5a has a polygonal shape. For example, the light detection region 5a has a hexagonal shape. When viewed from the Z-axis direction, the light detection region 5a is provided on an inner side in comparison to an outer edge of the image sensor 5. When viewed from the Z-axis direction, the light detection region 5a is provided on an inner side in comparison to the edges 54 and 55 of the first main surface 51 and the second main surface 52 of the image sensor 5. The light detection region 5a (pixel) is a charge generation region (a photosensitive region) in which charges are generated in response to incident light.

For example, a width of the light detection region 5a in the X-axis direction is 30 mm. For example, a width of the light detection region 5a in the Y-axis direction is 20 mm. The image sensor 5 captures an optical image by the light detection region 5a, and outputs an obtained image as an output image signal. The image sensor 5 is electrically connected to the wire disposed on the second main surface 42 of the support substrate 4 by a wire 14.

The FOP 6 covers the light detection region 5a of the image sensor 5. The FOP 6 includes a plurality of optical fibers. The plurality of optical fibers are two-dimensionally arranged with a predetermined arrangement pitch, and are bundled. The FOP 6 transmits the optical image by the plurality of optical fibers which are bundled. The FOP 6 includes an input end surface and an output end surface. The input end surface is constituted by an end surface on one side of the plurality of optical fibers. The output end surface is constituted by an end surface on the other side of the plurality of optical fibers. The FOP 6 transmits an optical image that is input from the input end surface and becomes an image capturing target to the output end surface.

The FOP 6 has a polygonal plate shape. The FOP 6 includes a first main surface 61, a second main surface 62, and a plurality of lateral surfaces 63. The first main surface 61 opposes the image sensor 5. The first main surface 61 has a polygonal shape. For example, the first main surface 61 has a hexagonal shape. The second main surface 62 opposes the scintillator 7. The second main surface 62 has a polygonal shape. For example, the second main surface 62 has a hexagonal shape. In this embodiment, the FOP 6 includes six lateral surfaces 63.

An edge 64 of the first main surface 61 and an edge 65 of the second main surface 62 overlap each other when viewed from the Z-axis direction. The edge 65 of the second main surface 62 is constituted by a plurality of corner portions 65a and a plurality of side portions 65b. Each of the plurality of side portions 65b connects the corner portions 65a adjacent to each other. The corner portions 65a are parts of the edge 65 of the second main surface 62. The corner portion 65a is linear segment having a predetermined length from the vertex of an angle of the edge 65 of the second main surface 62. Each of the lateral surfaces 63 connects the edge 64 of the first main surface 61 and the edge 65 of the second main surface 62. The lateral surfaces 63 adjacent to each other constitute a plurality of ridge portions 63a. In this embodiment, the edge 65 includes six corner portions 65a and six side portions 65b. In this embodiment, the FOP 6 includes six ridge portions 63a.

The corner portions 65a include a first corner portion 65c and a second corner portion 65d. The first corner portion 65c is located on the first direction D1 side. The second corner portion 65d is located on a second direction D2 side that is opposite to the first direction D1. For example, a length of the first corner portion 65c is 0.9 mm. For example, a length of the second corner portion 65d is 0.9 mm. In this embodiment, the corner portions 65a include two first corner portions 65c and four second corner portions 65d.

The ridge portions 63a include a first ridge portion 63c and a second ridge portion 63d. The first ridge portion 63c is located on the first direction D1 side. The second ridge portion 63d is located on the second direction D2 side. The first ridge portion 63c is constituted by the lateral surfaces 63 which are adjacent to the first corner portion 65c and are adjacent to each other. The second ridge portion 63d is constituted by the lateral surfaces 63 which are adjacent to the second corner portion 65d and are adjacent to each other. In this embodiment, the ridge portions 63a include two first ridge portions 63c and four second ridge portions 63d.

For example, a width of the FOP 6 in the X-axis direction is 33 mm. For example, a width of the FOP 6 in the Y-axis direction is 21.8 mm. For example, the thickness of the FOP 6 is 1.5 mm. The lateral surfaces 63 of the FOP 6 on the first direction D1 side are provided on an inner side in comparison to the lateral surfaces 53 of the image sensor 5 when viewed from the Z-axis direction. The other lateral surfaces 63 of the FOP 6 overlap the other lateral surfaces 53 of the image sensor 5 when viewed from the Z-axis direction.

The scintillator 7 is provided on the second main surface 62 and the plurality of lateral surfaces 63 of the FOP 6 to cover the light detection region 5a of the image sensor 5. The scintillator 7 spreads on the second main surface 62 of the FOP 6 and reaches the plurality of lateral surfaces 63 through the edge 65 of the second main surface 62. The scintillator 7 emits fluorescence (scintillation light) in accordance with incidence of radiation.

As illustrated in FIG. 5 and FIG. 6, the scintillator 7 reaches the lateral surfaces 63 from the second main surface 62 of the FOP 6 through the side portions 65b. The scintillator 7 is not provided in the first corner portion 65c and the second corner portion 65d of the FOP 6. As illustrated in FIG. 5 and FIG. 7, the scintillator 7 is provided on an inner side in comparison to the first corner portion 65c and the second corner portion 65d on the second main surface 62 of the FOP 6. The scintillator 7 is not provided in a region 65e that is sandwiched by the first corner portion 65c in the second main surface 62 of the FOP 6. The scintillator 7 is not provided in a region 65f that is sandwiched by the second corner portion 65d in the second main surface 62 of the FOP 6. The region 65e sandwiched by the first corner portion 65c in the second main surface 62 of the FOP 6 is exposed. The region 65f sandwiched by the second corner portion 65d in the second main surface 62 of the FOP 6 is exposed.

The scintillator 7 is not provided in the first ridge portion 63c and the second ridge portion 63d of the FOP 6. The scintillator 7 does not reach the first ridge portion 63c and the second ridge portion 63d on the lateral surfaces 63 of the FOP 6. The scintillator 7 is not provided in a region within a predetermined range from the first ridge portion 63c on the lateral surfaces 63 of the FOP 6. The scintillator 7 is not provided in a region within a predetermined range from the second ridge portion 63d on the lateral surfaces 63 of the FOP 6. The region within the predetermined range from the first ridge portion 63c on the lateral surfaces 63 of the FOP 6 is exposed. The region within the predetermined range from the second ridge portion 63d on the lateral surfaces 63 of the FOP 6 is exposed. For example, the region within the predetermined range from the first ridge portion 63c on the lateral surfaces 63 of the FOP 6 is a range up to a distance that is equal to a length of the first corner portion 65c from the first ridge portion 63c. For example, the region within the predetermined range from the second ridge portion 63d on the lateral surfaces 63 of the FOP 6 is a range up to a distance that is equal to a length of the second corner portion 65d from the second ridge portion 63d.

As described above, the scintillator 7 is provided on the second main surface 62 and the plurality of lateral surfaces 63 of the FOP 6 in such a manner that the respective corner portions 65a and the respective ridge portions 63a of the FOP 6 are exposed. The scintillator 7 is provided on the second main surface 62 and the plurality of lateral surfaces 63 of the FOP 6 in such a manner that the first corner portion 65c, the second corner portion 65d, the first ridge portion 63c, and the second ridge portion 63d are exposed. For example, the thickness of the scintillator 7 is 100 μm. The scintillator 7 is formed from a scintillator material. The scintillator material contains cesium iodide (CsI) such as CsI:Tl or CsI:Na as a main component. CsI has a structure in which a plurality of needle shaped crystals (columnar crystals) are forested.

The wiring substrate 11 is disposed on the first main surface 41 of the support substrate 4. The wiring substrate 11 is a printed substrate in which an electrode, a wire, and the like are disposed on a front surface. The electrode or the wire which is disposed on the front surface of the wiring substrate 11 is electrically connected to the wire disposed on the support substrate 4. That is, the electrode or the wire which is disposed on the wiring substrate 11 is electrically connected to the image sensor 5.

The wiring substrate 11 has a polygonal plate shape. When viewed from the Z-axis direction, respective lateral surfaces of the wiring substrate 11 overlap the lateral surfaces 43 of the support substrate 4. For example, the thickness of the wiring substrate 11 is 1 mm.

The IC 12 is disposed on the wiring substrate 11. The IC 12 is electrically connected to the image sensor 5 through the electrode or the wire which is disposed on the wiring substrate 11. The connector 13 is disposed on the wiring substrate 11. The connector 13 is electrically connected to the IC 12. The connector 13 is electrically connected to the signal cable 3. The connector 13 is electrically connected to one end of the wires of the signal cable 3. In this manner, in the signal cable 3, the one end of the wires is electrically connected to the image sensor 5 through the connector 13, and the like. The other end of the signal cable 3 is electrically connected to an external processing device.

The buffer material 9 is disposed between the structure and the case 8. The structure includes the image sensor 5, the FOP 6, and the scintillator 7. The buffer material 9 is in contact with the structure. The buffer material 9 is disposed at least between an end of the structure in the second direction D2, and the case 8. In this case, a gap (for example, a gap of 500 μm) in which the buffer material 9 is disposed is provided between the end of the structure in the second direction D2 and the case 8. The buffer material 9 may be disposed over the entire periphery of the structure including the image sensor 5, the FOP 6, and the scintillator 7 when viewed from the Z-axis direction. In this case, a gap (for example, a gap of 200 μm) in which the buffer material 9 is disposed is further provided between both sides of the structure in the Y-axis direction, and the case 8. For example, a material of the buffer material 9 is silicone rubber or the like.

The intraoral sensor 1 configured as described above is inserted into an oral cavity of a patient, and is disposed in such a manner that the detection surface 21 of the main body portion 2 opposes a radiation source disposed at the outside of the oral cavity through teeth or gums. When radiation is radiated from the radiation source, the radiation is transmitted through the teeth or the gums and is incident to the scintillator 7. The scintillator 7 emits fluorescence in correspondence with the intensity of the incident radiation. The fluorescence is transferred to the light detection region 5a of the image sensor 5 by the FOP 6, and is converted into an electric signal in the image sensor 5. The electric signal converted in the image sensor 5 is transmitted to a PC through the wire 14, the support substrate 4, the wiring substrate 11, the signal cable 3, and the like. The electric signal is converted into a fluoroscopic image of the teeth or the gums in the PC.

As described above, in the intraoral sensor 1, the scintillator 7 is provided on the second main surface 62 and the plurality of lateral surfaces 63 in such a manner that the first corner portion 65c and the second corner portion 65d, and the first ridge portion 63c and the second ridge portion 63d of the FOP 6 are exposed. That is, the scintillator 7 is not located on the first corner portion 65c and the second corner portion 65d, and the first ridge portion 63c and the second ridge portion 63d of the FOP 6. Accordingly, even in a case where a portion on the first direction D1 side and on the second direction D2 side in the case 8 receive impact from the outside, the impact is less likely to be transferred to the scintillator 7, and thus the scintillator 7 is less likely to be peeled off. As a result, it is not necessary to enlarge an external shape of the case 8 to suppress peeling-off of the scintillator 7, and thus an increase in size of the intraoral sensor 1 is suppressed. As described above, the scintillator 7 is less likely to be peeled off, and thus reliability of the intraoral sensor 1 is improved.

As in the intraoral sensor 1, in a case where the scintillator 7 is provided also in the lateral surfaces 63 of the FOP 6, impact from the outside of the intraoral sensor 1 is likely to be transferred to the scintillator 7. According to this, the scintillator 7 is likely to be peeled off from the first corner portion 65c, the second corner portion 65d, the first ridge portion 63c, and the second ridge portion 63d of the FOP 6. In the intraoral sensor 1, as described above, since the scintillator 7 is not located on the first corner portion 65c, the second corner portion 65d, the first ridge portion 63c, and the second ridge portion 63d of the FOP 6, the scintillator 7 is less likely to be peeled off from the FOP 6. That is, in a case where the scintillator 7 is also provided on the lateral surfaces 63 of the FOP 6, the above-described effect in which the scintillator 7 is less likely to be peeled off becomes particularly remarkable.

In the intraoral sensor 1, the scintillator 7 is formed from the scintillator material that contains CsI as a main component. In this case, the scintillator 7 can be formed by vapor deposition, and thus it is possible to easily provide the scintillator 7. CsI has a structure in which a plurality of needle shaped crystals are forested. Light emitted by the needle shaped crystals is less likely to spread to the periphery in comparison to granular crystals. According to this, light emitted by the needle shaped crystals is more accurately transferred to positions of the image sensor 5 which correspond to the needle shaped crystals. Accordingly, it is possible to improve resolution of an image of the image sensor 5.

In the intraoral sensor 1, the buffer material 9 is disposed between the end of the structure in the second direction D2 and the case 8. The structure includes the image sensor 5, the FOP 6, and the scintillator 7. According to this configuration, impact which the intraoral sensor 1 receives from the outside is less likely to be transferred to the scintillator 7. Accordingly, peeling-off of the scintillator 7 is more reliably suppressed.

Figure 8:
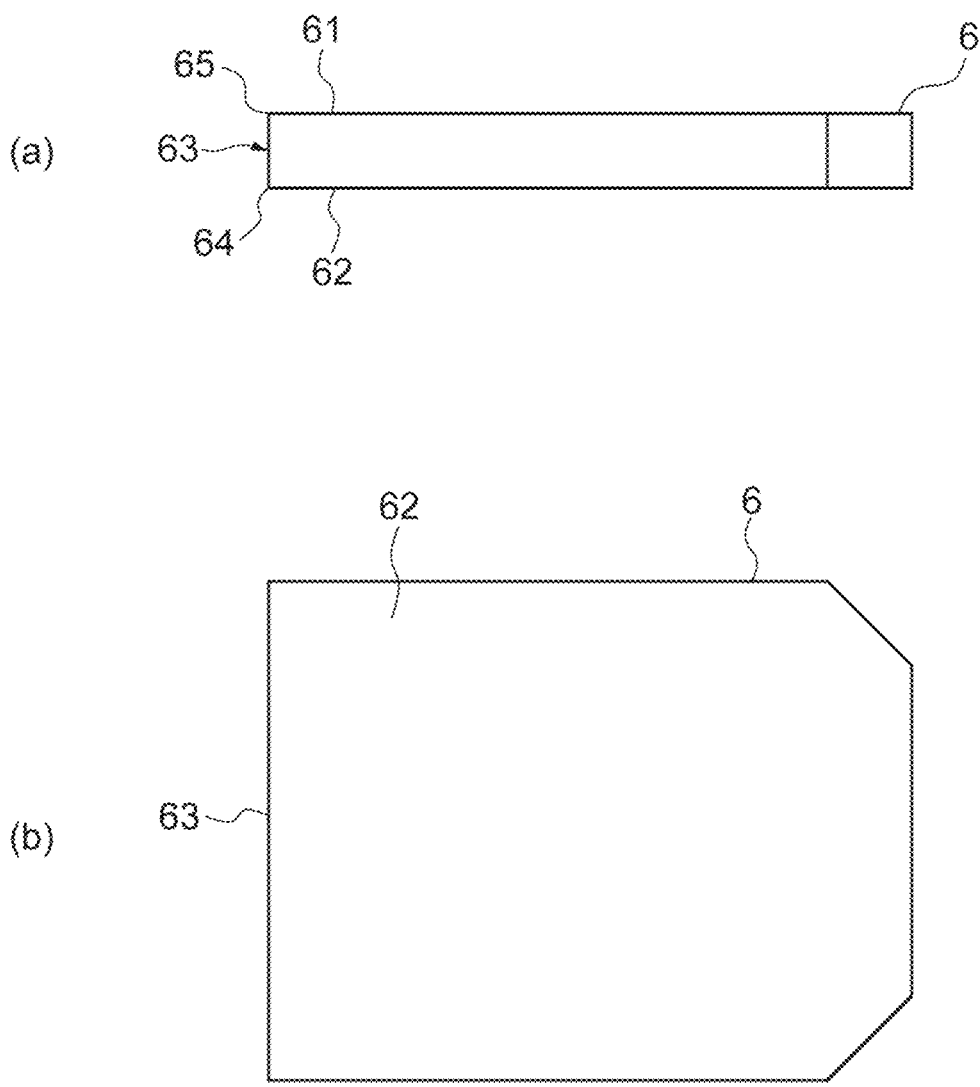
FIG. 8 is a view illustrating a method for manufacturing the intraoral sensor.
Figure 9:
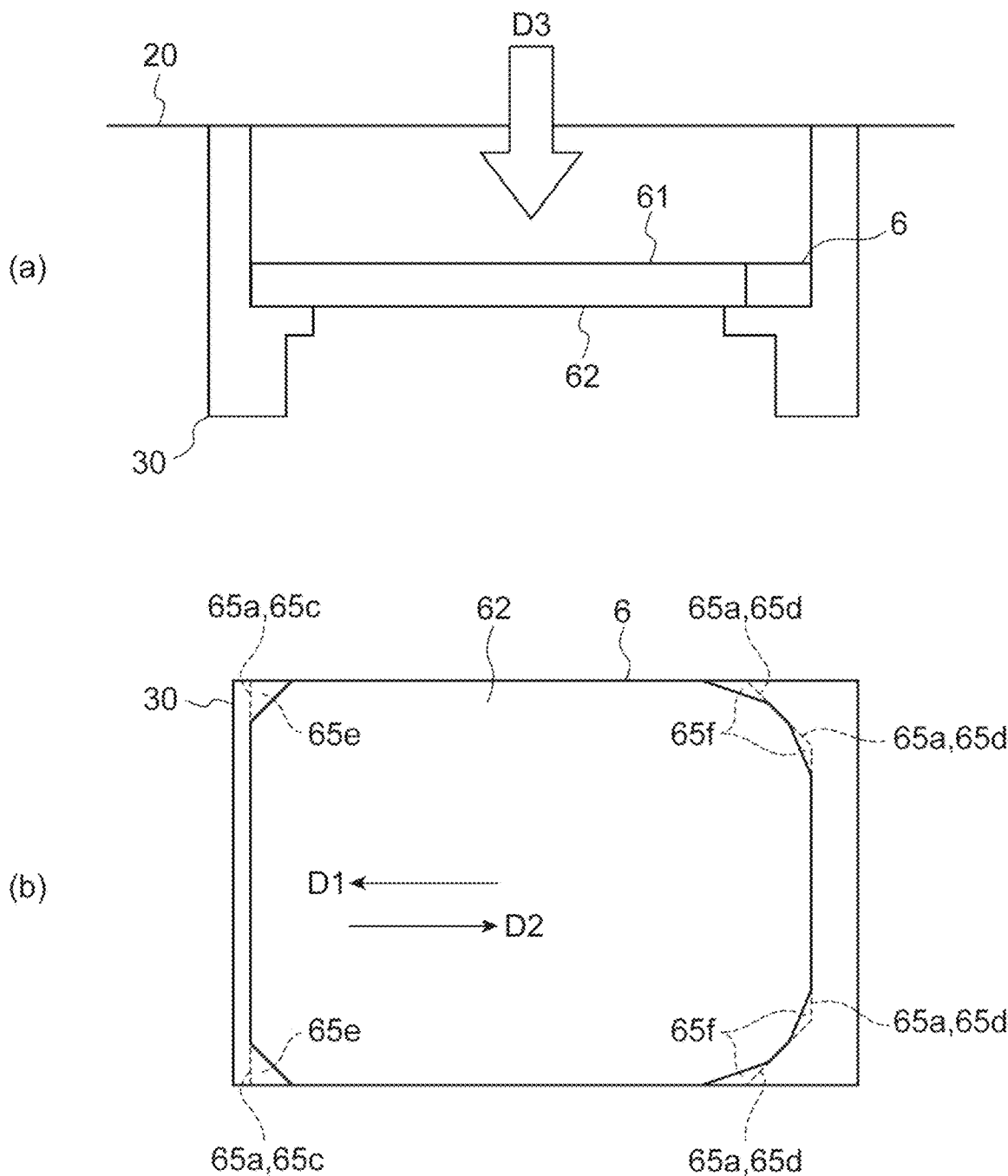
FIG. 9 is a view illustrating the method for manufacturing the intraoral sensor.

Next, the method for manufacturing the intraoral sensor 1 according to this embodiment will be described with reference to FIG. 8 to FIG. 11. FIG. 8 to FIG. 11 are views illustrating the method for manufacturing the intraoral sensor 1. In FIG. 8 and FIG. 9, (a) is a front view and (b) is a bottom view. As illustrated in FIG. 8, first, FOP 6 is prepared. Next, as illustrated in FIG. 9, the FOP 6 is placed on a jig 30 that is disposed inside a chamber 20 along a direction D3. The jig 30 has a shape that covers the respective corner portions 65a of the FOP 6. The jig 30 has a shape that covers the region 65e sandwiched by the first corner portion 65c, and the region 65f sandwiched by the second corner portion 65d in the second main surface 62 of the FOP 6.

Figure 10:
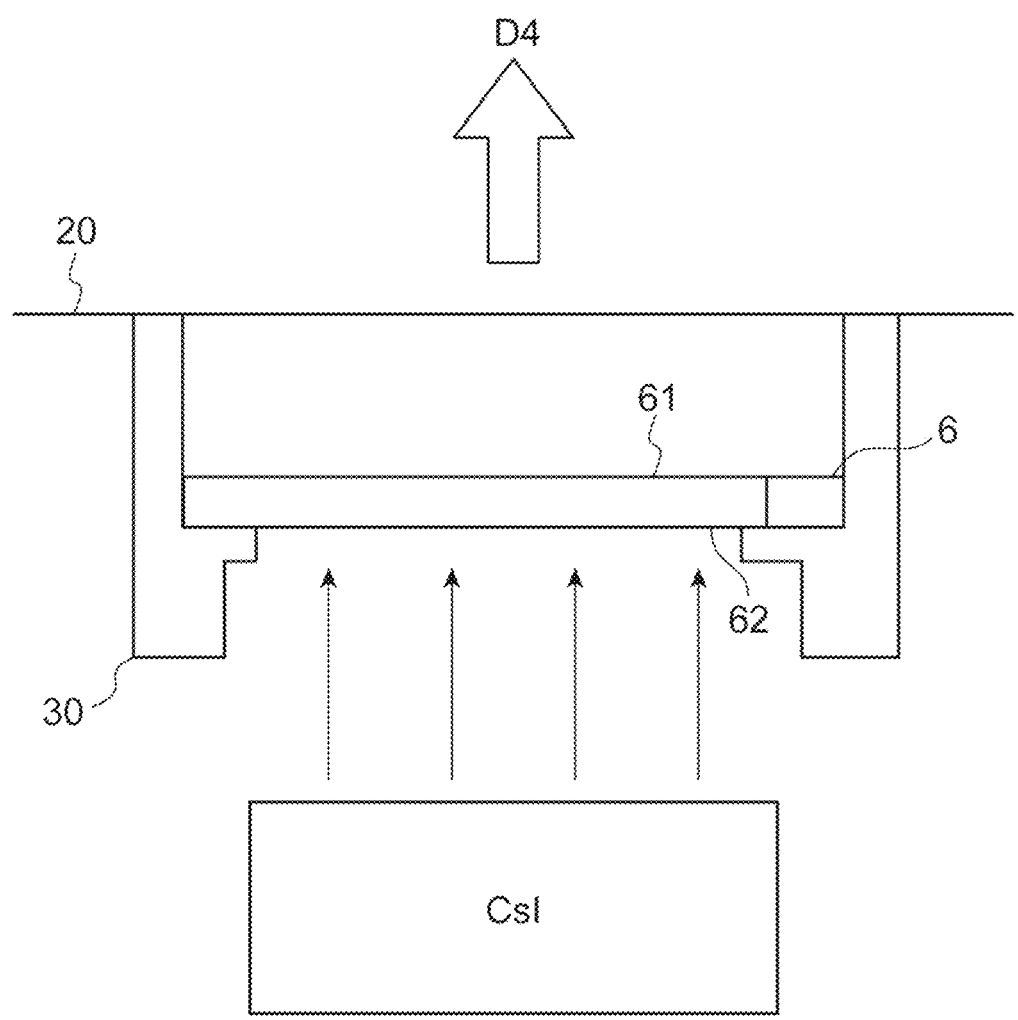
FIG. 10 is a view illustrating the method for manufacturing the intraoral sensor.
Figure 11:
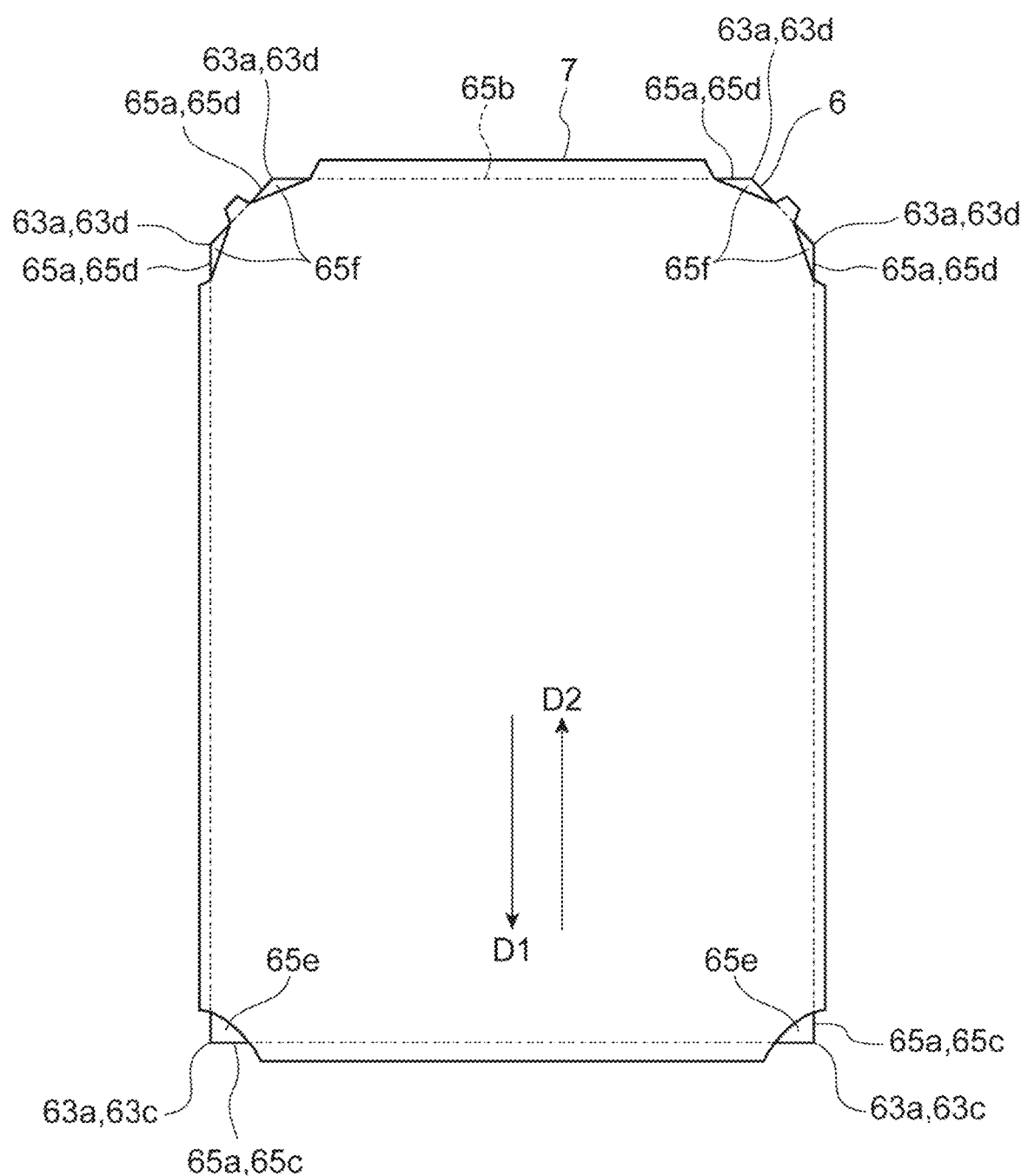
FIG. 11 is a view illustrating the method for manufacturing the intraoral sensor.

Next, as illustrated in FIG. 10, the scintillator 7 is provided. Specifically, the scintillator 7 is provided on the second main surface 62 and the plurality of lateral surfaces 63 in such a manner that the first corner portion 65c, the second corner portion 65d, the first ridge portion 63c, and the second ridge portion 63d of the FOP 6 are exposed. When providing the scintillator 7, the first corner portion 65c and the second corner portion 65d are covered with the jig 30 that supports the FOP 6. In addition, the scintillator material that constitutes the scintillator 7 is vapor deposited with the jig 30 as a mask. At this time, the scintillator 7 is also vapor deposited on the lateral surfaces 63 which constitute the side portions 65b of the FOP 6. The scintillator material contains CsI as a main component. Next, the FOP 6 is peeled off from the jig 30 along a direction D4. As a result, as illustrated in FIG. 11, the FOP 6 on which the scintillator 7 is vapor deposited is obtained.

Next, the FOP 6 on which the scintillator 7 is vapor deposited is disposed on the image sensor 5 that is disposed on the support substrate 4. The support substrate 4 is a substrate that supports the image sensor 5 in a process of manufacturing the image sensor 5. Next, the support substrate 4, the image sensor 5, the FOP 6, and the scintillator 7 are contained in a first case 81 of the case 8. At this time, the wiring substrate 11 on which the IC 12 and the connector 13 are disposed are contained in the first case 81 in advance.

Next, the support substrate 4 and the wiring substrate 11 are fixed. At this process, the wire disposed on the support substrate 4, and the electrode or the wire that is disposed on the wiring substrate 11 are electrically connected to each other. Next, the wire disposed on the support substrate 4 and the image sensor 5 are electrically connected by the wire 14. Next, a second case 82 engages with the first case 81. Next, the signal cable 3 is mounted and fixed to the fixing portion 83 of the case 8, and is electrically connected to the connector 13.

As described above, according to the method for manufacturing the intraoral sensor 1, the scintillator 7 is provided on the second main surface 62 and the plurality of lateral surfaces 63 in such a manner that the first corner portion 65c, the second corner portion 65d, the first ridge portion 63c, and the second ridge portion 63d of the FOP 6 are exposed.

Accordingly, as described above, the intraoral sensor 1 in which an increase in size is suppressed and reliability is improved is obtained.

In the method for manufacturing the intraoral sensor 1, when providing the scintillator 7, the first corner portion 65c and the second corner portion 65d are covered with the jig 30 that supports the FOP 6, and the scintillator material that constitutes the scintillator 7 is vapor deposited with the jig 30 as a mask. According to this, the process of manufacturing the intraoral sensor 1 is simplified.

In the method for manufacturing the intraoral sensor 1, the scintillator material contains CsI as a main component. In this case, formation of the scintillator 7 by the vapor deposition becomes simple.

Hereinbefore, description has been given of an embodiment of the invention, but the invention is not limited to the above-described embodiment.

Figure 12:
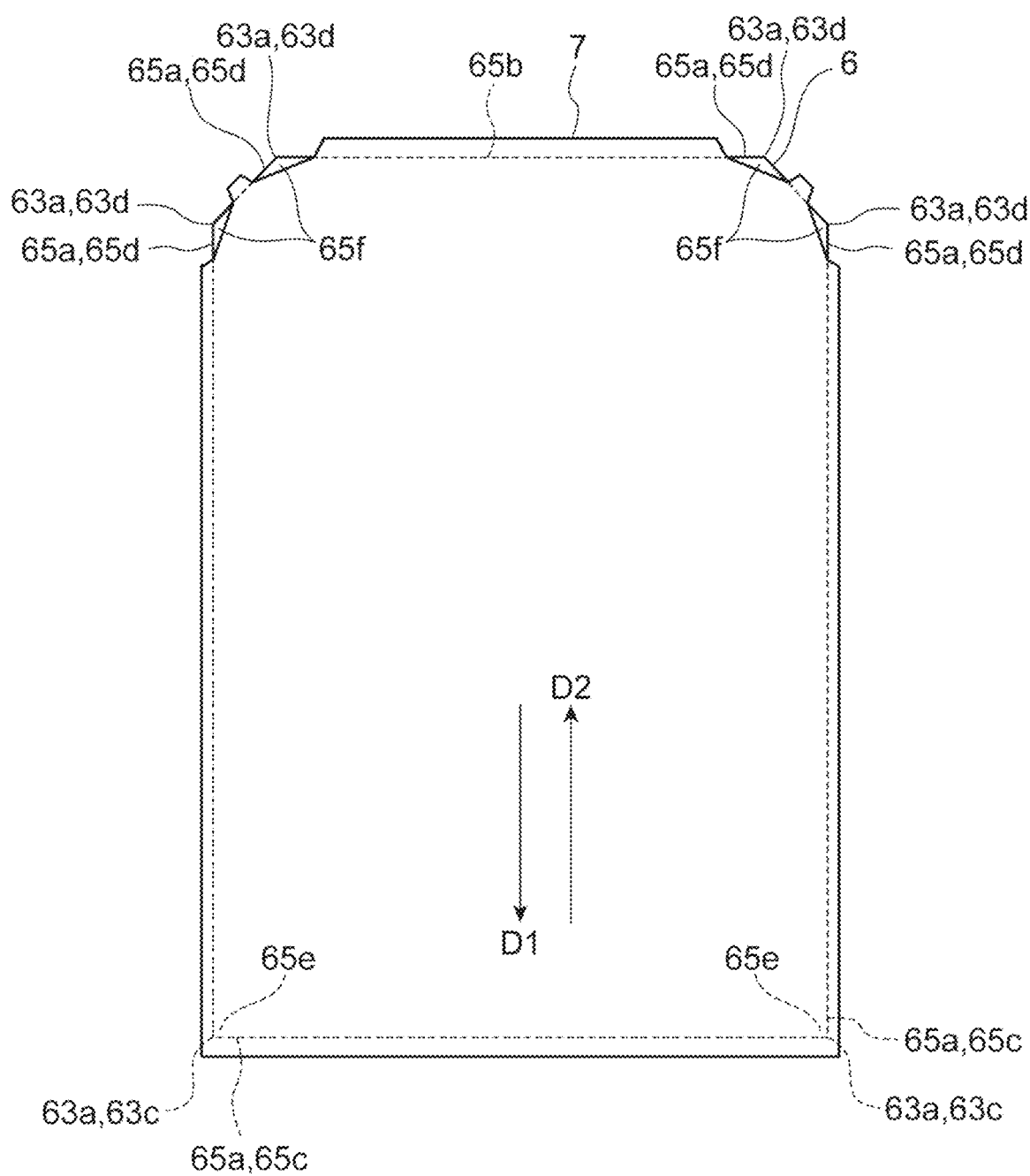
FIG. 12 is a view illustrating a modification example of the intraoral sensor.

As illustrated in FIG. 12, the scintillator 7 may be provided in the first corner portion 65c and the first ridge portion 63c of the FOP 6. The scintillator 7 only have to be provided on the second main surface 62 and the plurality of lateral surfaces 63 of the FOP 6 in such a manner that the second corner portion 65d out of the plurality of corner portions 65a of the FOP 6 and the second ridge portion 63d out of the plurality of ridge portions 63a are exposed.

In the method for manufacturing the intraoral sensor 1, the scintillator 7 may be provided on the first corner portion 65c and the first ridge portion 63c of the FOP 6. In the method for manufacturing the intraoral sensor 1, the scintillator 7 only have to be provided on the second main surface 62 and the plurality of lateral surfaces 63 of the FOP 6 in such a manner that the second corner portion 65d out of the plurality of corner portions 65a of the FOP 6 and the second ridge portion 63d out of the plurality of ridge portions 63a are exposed.

Figure 13:
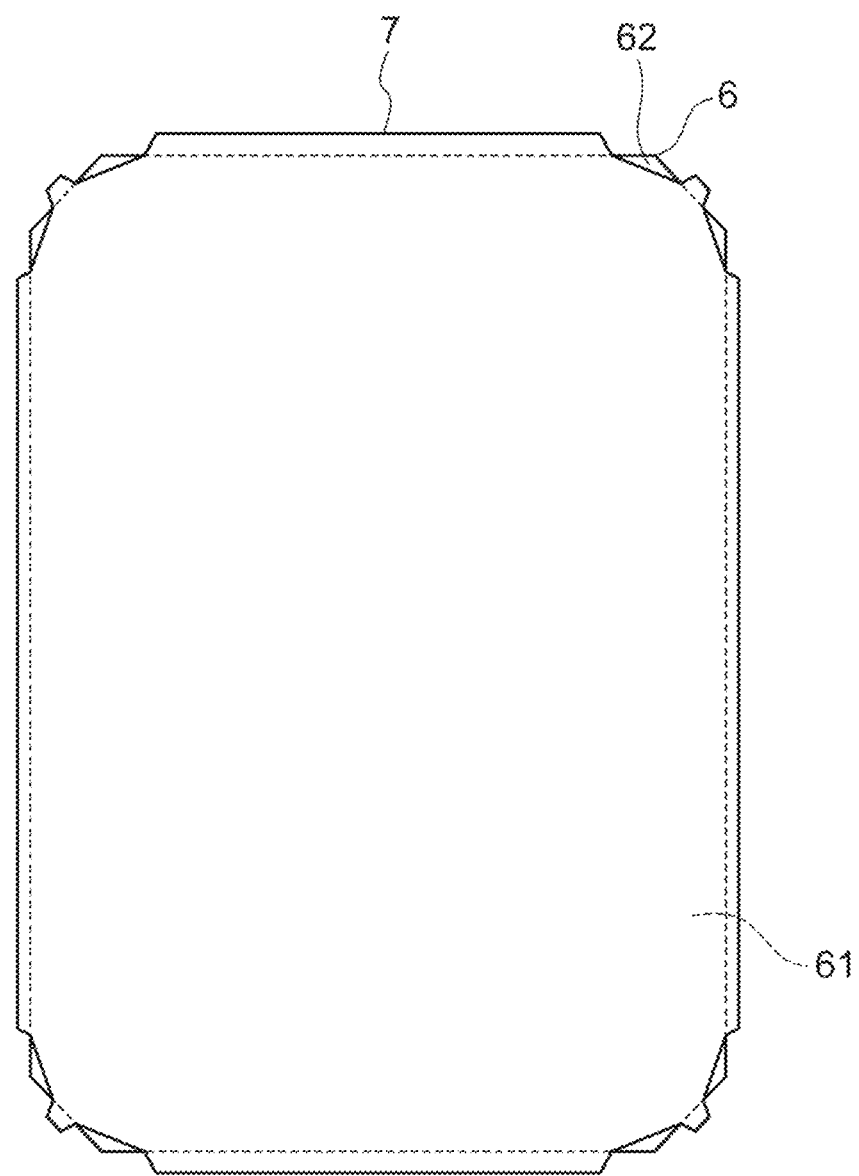
FIG. 13 is a view illustrating a modification example of the intraoral sensor.

The first main surface 61 and the second main surface 62 of the FOP 6 may not have the hexagonal shape. The first main surface 61 and the second main surface 62 of the FOP 6 only have to have a polygonal shape. As illustrated in FIG. 13, for example, the first main surface 61 and the second main surface 62 of the FOP 6 may have an octagonal shape.

The first main surface 51 and the second main surface 52 of the image sensor 5 may not have the hexagonal shape. The first main surface 51 and the second main surface 52 of the image sensor 5 may have a polygonal shape. For example, the first main surface 51 and the second main surface 52 of the image sensor 5 may have an octagonal shape.

The first main surface 41 and the second main surface 42 of the support substrate 4 may not have the hexagonal shape. The first main surface 41 and the second main surface 42 of the support substrate 4 may have a polygonal shape. For example, the first main surface 41 and the second main surface 42 of the support substrate 4 may have an octagonal shape.

The scintillator 7 may not be provided in the entirety of a region except for the ridge portions 63a in the lateral surfaces 63 of the FOP 6. The scintillator 7 may not be provided in a part of the region except for ridge portions 63a in the lateral surfaces 63 of the FOP 6. A part of the region except for the ridge portions 63a in the lateral surfaces 63 of the FOP 6 may be exposed.

Figure 14:
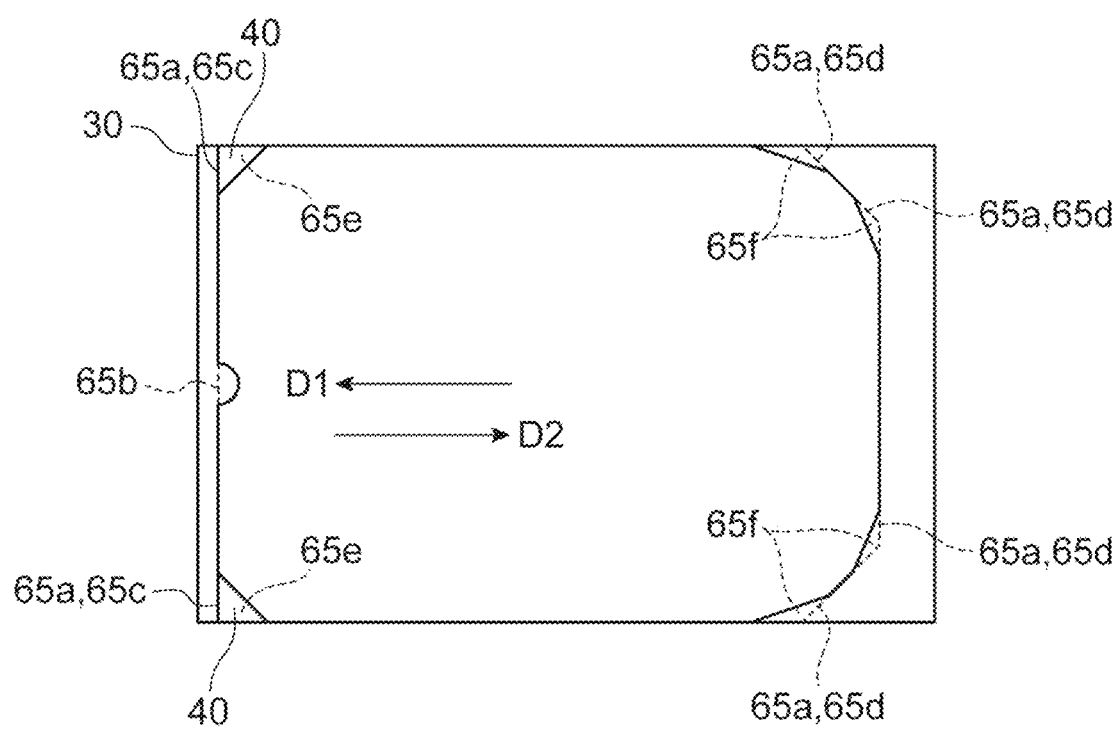
FIG. 14 is a view illustrating a modification example of the method for manufacturing the intraoral sensor.

In the method for manufacturing the intraoral sensor 1, when providing the scintillator 7, the first corner portion 65c may not be covered with the jig 30 that supports the FOP 6. In the method for manufacturing the intraoral sensor 1, when providing the scintillator 7, the second corner portion 65d out of the plurality of corner portions 65a of the FOP 6 may be covered, and the scintillator material that constitutes the scintillator 7 may be vapor deposited with the jig 30 as a mask. As illustrated in FIG. 14, the jig 30 may cover a part of the corner portions 65a (for example, the second corner portion 65d) and a part of the side portions 65b of the FOP 6, and may support the FOP 6. At this time, another corner portion 65a (for example, the first corner portion 65c) of the FOP 6 may be covered with a mask 40. A position of the part of the side portion 65b which is covered with and is supported by the jig 30 can be set to various positions on the side portions 65b. For example, the part of the side portion 65b may be located on any side portion 65b out of the side portions 65b between the corner portions 65a adjacent to each other.

REFERENCE SIGNS LIST

1: intraoral sensor, 3: signal cable, 5: image sensor, 5a: light detection region, 6: FOP, 7: scintillator, 8: case, 9: buffer material, 30: jig, 40: mask, 61: first main surface, 62: second main surface, 63: lateral surface, 63a: ridge portion, 64, 65: edge, 65a: corner portion, 65b: side portion, D1: first direction, D2: second direction.

The invention claimed is:

1. An intraoral sensor comprising:
an image sensor including a light detection region;
a fiber optical plate disposed on the image sensor to cover the light detection region;
a scintillator disposed on the fiber optical plate;
a case containing the image sensor, the fiber optical plate, and the scintillator; and
a signal cable electrically connected to the image sensor and extending beyond from the case,
wherein the fiber optical plate includes,
a first main surface opposing the image sensor and having a polygonal shape,
a second main surface opposing the scintillator and having a polygonal shape, and
a plurality of lateral surfaces connecting an edge of the first main surface and an edge of the second main surface, wherein
the edge of the second main surface includes a plurality of corner portions, and a plurality of side portions connecting the corner portions adjacent to each other, and
the scintillator is provided on the second main surface and the plurality of lateral surfaces in such a manner that a corner portion located on a second direction side opposite to a first direction in which the signal cable extending beyond out of the plurality of corner portions and a ridge portion are exposed, the ridge portion constituted by the lateral surfaces adjacent to the corner portion located on the second direction side and adjacent to each other.

2. The intraoral sensor according to claim 1,
wherein the scintillator is provided on the second main surface and the plurality of lateral surfaces in such a manner that a corner portion located on the first direction side out of the plurality of corner portions and a ridge portion are also exposed, the ridge portion constituted by the lateral surfaces adjacent to the corner portion located on the first direction side and adjacent to each other.

3. The intraoral sensor according to claim 1,
wherein the scintillator is formed from a scintillator material containing CsI as a main component.

4. The intraoral sensor according to claim 1, further comprising:
a buffer material disposed between an end of a structure in the second direction and the case, and contacting with the structure, the structure including the image sensor, the fiber optical plate, and the scintillator.

5. A method for manufacturing an intraoral sensor, the intraoral sensor including a structure including an image sensor, a fiber optical plate, and a scintillator, a case containing the structure, and a signal cable electrically connected to the image sensor and extending beyond from the case, the method comprising:
preparing the fiber optical plate including a first main surface having a polygonal shape, a second main surface opposite to the first main surface and having a polygonal shape, and a plurality of lateral surfaces connecting an edge of the first main surface and an edge of the second main surface, the edge of the second main surface being constituted by a plurality of corner portions and a plurality of side portions connecting the corner portions adjacent to each other; and
providing the scintillator on the second main surface and the plurality of lateral surfaces in such a manner that a corner portion located on a second direction side opposite to a first direction in which the signal cable extending beyond out of the plurality of corner portions and a ridge portion are exposed, the ridge portion constituted by the lateral surfaces adjacent to the corner portion located on the second direction side and adjacent to each other.

6. The method for manufacturing an intraoral sensor according to claim 5,
wherein when providing the scintillator,
covering the corner portion located on the second direction side with a jig supporting the fiber optical plate, and
vapor depositing a scintillator material constituting the scintillator with the jig as a mask.

7. The method for manufacturing an intraoral sensor according to claim 6,
wherein the scintillator material contains CsI as a main component.

* * * * *